(12) United States Patent
Chou et al.

(10) Patent No.: US 10,139,383 B2
(45) Date of Patent: Nov. 27, 2018

(54) REAL-TIME AIR MONITORING WITH MULTIPLE SENSING MODES

(71) Applicant: TricornTech Taiwan, Taipei (TW)

(72) Inventors: Tsung-Kuan A. Chou, San Jose, CA (US); Li-Peng Wang, Taipei (TW)

(73) Assignee: TricornTech Taiwan, Taipei (TW)

( * ) Notice: Subject to any disclaimer, the term of this patent is extended or adjusted under 35 U.S.C. 154(b) by 660 days.

(21) Appl. No.: 14/555,942

(22) Filed: Nov. 28, 2014

(65) Prior Publication Data

US 2015/0153299 A1    Jun. 4, 2015

Related U.S. Application Data

(60) Provisional application No. 61/910,910, filed on Dec. 2, 2013.

(51) Int. Cl.
*G01N 1/00* (2006.01)
*G01N 33/00* (2006.01)
*G01N 30/78* (2006.01)

(52) U.S. Cl.
CPC ......... *G01N 33/0075* (2013.01); *G01N 30/78* (2013.01)

(58) Field of Classification Search
CPC ....................................................... G01N 1/00
See application file for complete search history.

(56) References Cited

U.S. PATENT DOCUMENTS 5,832,411 A    11/1998  Schatzmann et al.
6,981,947 B2    1/2006   Melker 7,227,136 B2    6/2007  Walte et al.
2003/0071629 A1  4/2003  Yang et al.
2004/0245993 A1  12/2004 Bonne
2013/0046485 A1  2/2013  Norman et al.

FOREIGN PATENT DOCUMENTS

CN         1759312 A      4/2006
CN       101299031 A     11/2008
(Continued)

OTHER PUBLICATIONS

ROC (Taiwan) Pat. App. No. 201480071789.8—First Office Action with English Translation, dated Dec. 9, 2017, 15 pages.
(Continued)

*Primary Examiner* — Jyoti Nagpaul
(74) *Attorney, Agent, or Firm* — Womble Bond Dickinson (US) LLP

(57) ABSTRACT

Embodiments of a gas detector with a first gas sensor having a first gas specificity and a first response time and a second gas sensor having a second gas specificity and a second response time. The first gas specificity is different than the second gas specificity, the first response time is different than the second response time, or both the first gas specificity and the first response time are different than the second gas specificity and the second response time. A readout and analysis circuit is coupled to the first and second gas sensors to read and analyze data from the first and second gas sensors, and a control circuit is coupled to the readout and analysis circuit and to the first and second gas sensors to execute logic that operates the first gas sensor, the second gas sensor, or both the first and second gas sensors.

15 Claims, 14 Drawing Sheets

(56) References Cited

FOREIGN PATENT DOCUMENTS

| TW | 201132977 A | 10/2011 | |
|---|---|---|---|
| WO | WO-2011005882 A2 * | 1/2011 | ............. G01N 30/30 |

OTHER PUBLICATIONS

PCT/US2014/068108—PCT International Preliminary Report on Patentability and Written Opinion, dated Jun. 16, 2016, 8 pages.
PCT/US2014/068108—PCT International Search Report and Written Opinion, dated Mar. 19, 2015, 13 pages.
Extended European Search Report for counterpart EP Patent Application No. 14868017.6, dated Jun. 28, 2017, 7 pgs.
Mara Bernabei, et al., "Large-Scale Chemical Sensor Array Testing Biological Olfaction Concepts," XP011468823, IEEE Sensors Journal, vol. 12, No. 11, pp. 3174-3183 (Nov. 1, 2012).
First Office Action for counterpart ROC (Taiwan) Patent Application No. 103141844 with English translation, 16 pgs., dated Apr. 16, 2018.
First Office Action for counterpart Chinese Patent Application No. 201480071789.8 with English translation, dated Dec. 9, 2017, 15 pages.
Second Office Action for counterpart Chinese Patent Application No. 201480071789.8 with English translation, dated Oct. 26, 2017, 5 pages.
Third Office Action for counterpart Chinese Patent Application No. 201480071789.8 with English translation, dated May 4, 2018, 12 pages.

* cited by examiner

REAL-TIME AIR MONITORING WITH MULTIPLE SENSING MODES

CROSS-REFERENCE TO RELATED APPLICATIONS

This application claims priority under 35 U.S.C. § 119(e) to U.S. Provisional Application No. 61/910,910, filed 2 Dec. 2013. The priority provisional is hereby incorporated herein by reference in its entirety.

TECHNICAL FIELD

The disclosed embodiments relate generally to gas sensing and in particular, but not exclusively, to real-time air monitoring with multiple sensing modes.

BACKGROUND

Gas detection and analysis can be an important means for detecting the presence and concentration of certain chemicals in the environment and determining the meaning of the particular combination of chemicals present. For example, gas analysis can be used to determine the presence of dangerous substances incompatible with human presence, such as methane, carbon monoxide or carbon dioxide in a mine. But existing gas detection and analysis systems usually involve a tradeoff between speed and gas specificity, which is the ability to identify particular gases in a sample. Fast detectors are not specific enough, and high-specificity detectors are not fast enough.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION OF ILLUSTRATED EMBODIMENTS

Figure 1A:
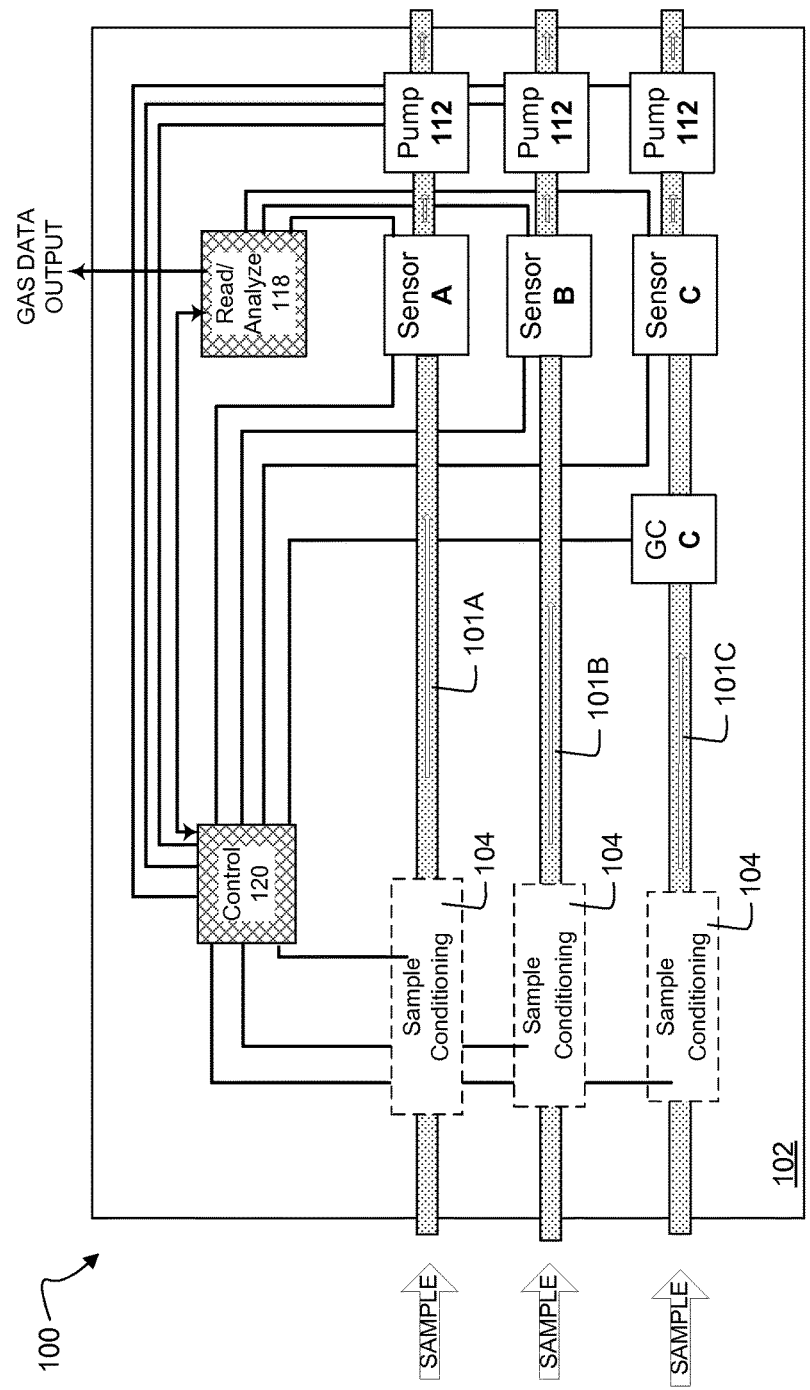
FIG. 1A-1D are block diagrams of embodiments of a gas detector using multiple gas detection systems.

Embodiments are described of an apparatus, system and method for real-time air monitoring with multiple sensing modes. Specific details are described to provide a thorough understanding of the embodiments, but one skilled in the relevant art will recognize that the described embodiments can be practiced without one or more of the described details, or with other methods, components, materials, etc. In some instances, well-known structures, materials, or operations are not shown or described in detail but are nonetheless encompassed within the scope of the invention.

Reference throughout this specification to "one embodiment" or "an embodiment" means that a described feature, structure, or characteristic can be included in at least one described embodiment, so that appearances of "in one embodiment" or "in an embodiment" do not necessarily all refer to the same embodiment. Furthermore, the particular features, structures, or characteristics may be combined in any suitable manner in one or more embodiments.

Embodiments are disclosed of a method/apparatus of monitoring real-time ambient air quality by a combination of multiple gas analysis sensing modes, including fast-response gas sensors with low specificity to single compound (e.g., photoionization detector (PID), thermal conductivity detector (TCD), flame ionization detector (FID), time-of-flight mass spectrometer (TOFMS)) and slow-response gas detectors with high specificity to each compound of interest (e.g., gas chromatograph (GC)+PID, GC+TCD, GC+FID, GC+mass spectrometer (MS)). The gas detection modes can be operated independently (one at a time or simultaneously in parallel) or in certain sequences based on sensing criteria.

The disclosed embodiments can be used for gas sensing in various indoor or outdoor environmental setups. In a semiconductor facility, the disclosed embodiments can be used to ensure cleanroom air quality, ensuring the air is free of contaminants and improving process yield. In a steel manufacturing facility, the disclosed embodiments can be used to monitor the coke oven gas by-product leakage and process optimization. In a petrochemical facility, the disclosed embodiments can be used to identify leaking gases and locate the source of leakage, which can provide immediate warning and emergency response actions.

FIG. 1 illustrates an embodiment of a gas detection detector 100. Gas detection detector 100 includes a substrate 102 on which are mounted several components. Gas sensor A is mounted on substrate 102 with its inlet coupled to optional sample conditioning unit 104 by fluid connection 101A and its outlet coupled to a pump 112. Detector 100 includes gas sensor B, similarly arranged as gas sensor A, and gas sensor C which is similarly arranged to gas sensors A and B except that a gas chromatograph (GC) C is coupled in fluid connection 101C between optional sample conditioner 104 and gas sensor C. A controller or control circuit 120 is coupled to all sample conditioners 104, to sensors A-C, to pumps 112, and to gas chromatograph C. Readout and analysis circuit 118 is coupled to sensors A-C and also to control circuit 120.

Substrate 102 can be any kind of substrate that provides the required physical support for the elements of gas detector 100. In one embodiment, substrate 102 can be a single-layer printed circuit board (PCB) with conductive traces on its surface, but in other embodiments it can be a multi-layer PCB with conductive traces in the interior of the circuit board. In other embodiments, for example an embodiment where device 100 is built as a monolithic system on a single die, substrate 102 can be chip or wafer made of silicon or some other semiconductor. In still other embodiments, substrate 102 can also be a chip or wafer in which optical waveguides can be formed to support optical communication between the components of device 100. And in still other embodiments the elements need not be formed on a common substrate at all.

Figure 1B:
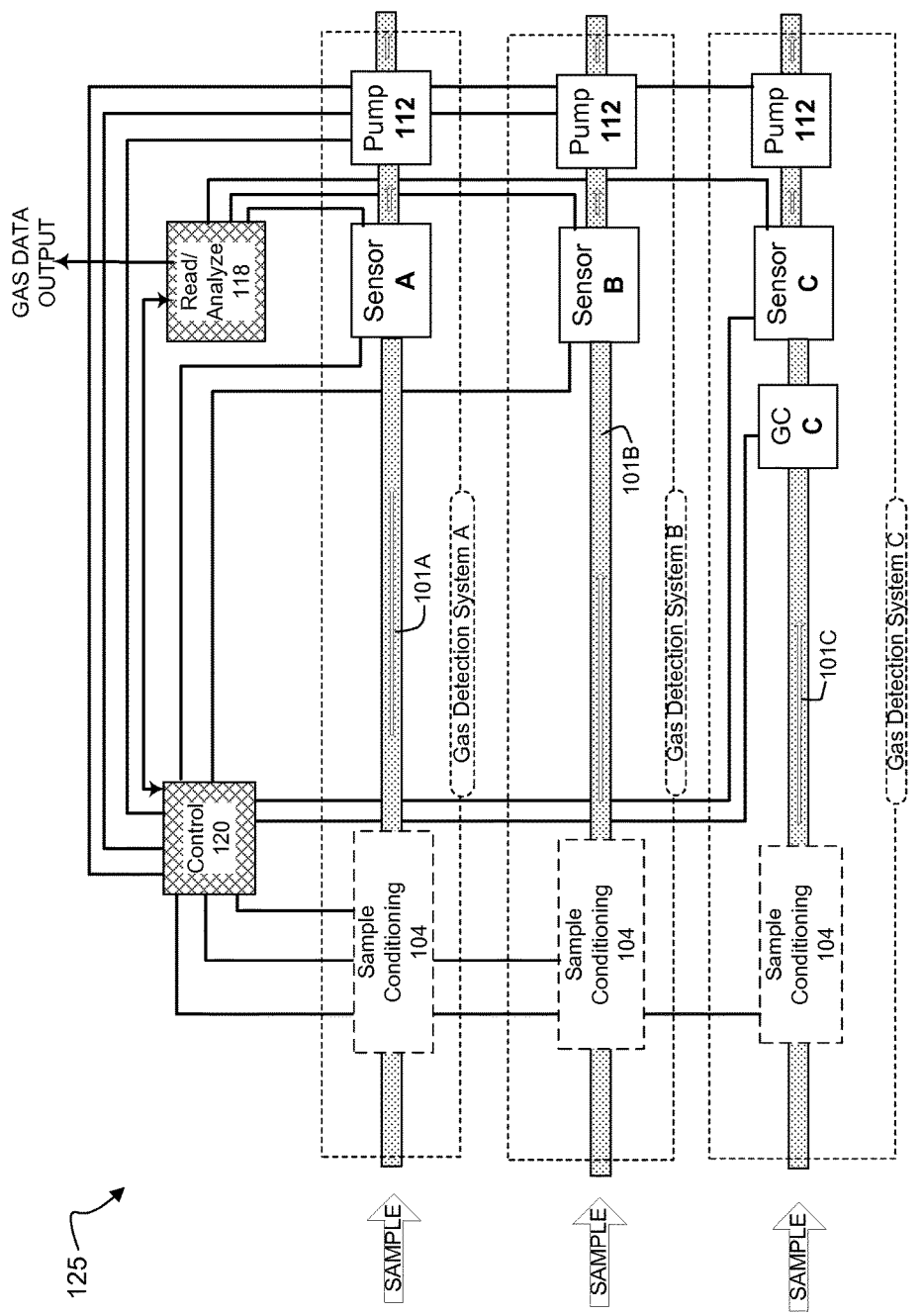

Gas detector 100 includes first, second, and third gas sensors: first gas sensor A is a Mode A gas sensor, second gas sensor B is a Mode B gas sensor, and third gas sensor C is a Mode C gas sensor. As used herein, the terms "gas sensor," "gas detector," or "gas detection system" can be used to refer to a gas sensor on its own or to a gas sensor in combination with other elements—such as a gas chromatograph, for instance—or as a separate gas detection system such as gas detection systems A-C shown in FIGS. 1A-1D. In FIG. 1B, for example, sensor C is coupled to gas chromatograph C, but is designated separately; nonetheless, the combination of sensor C with gas chromatograph C, as well as other components present, can together be referred to as gas detection system C.

Mode A sensors are real-time universal gas sensors with little or no specificity to a single compound or to compounds with same or similar chemical property. Possible mode A sensors include, for example, photoionization detector (PID) sensors, thermal conductivity detector (TCD) sensors, and flame ionization detector (FID) sensors, but are not limited to these. Embodiments of mode A gas sensors can detect the total concentration of gases in the environment (organic or non-organic) with real-time response (less than 1 minute in one embodiment, but not limited to this time period), but mode A detectors lack specificity to detect certain group of compounds or individual compounds separately.

Mode B sensors are fast-response gas sensors with little or no specificity to a single compound, but with partial specificity so that it can differentiate compounds with the same or similar chemical properties from other compounds with different chemical properties. In different embodiments the Mode B sensors can be, for example, electrochemical sensors, metal oxide sensors, IR sensors, and e-nose sensors, but embodiments are not limited to these. Mode B sensors can detect the total concentration of certain group of gases in the environment (organic or non-organic) with fast response time (from 1 to 10 minutes in one embodiment, but not limited to such a time period), but the Mode B detectors lack the specificity to detect individual compounds separately.

Mode C sensors are slow-response gas sensors with high specificity to single compounds that require longer analysis time. In different embodiments the Mode C sensors can be, for example, gas chromatograph plus flame ionization (GC+FID), gas chromatograph plus mass spectrometer (GC+MS), gas chromatograph plus thermal conductivity detector (GC+TCD), and ion separation+MS, but are not limited to these. Embodiments of mode C detector can detect and analyze each individual compound of interest but requires a relatively longer detection time (from 10 minutes to 120 minutes in one embodiment, but not limited to this time period).

Pumps 112 are coupled to the fluid outlets of detectors A, B, and C so that the pumps draw the gas sample into and through detectors A, B, and C and return the sample to the atmosphere. Pumps 112 can be any kind of pump that meets the size and form factor requirements of detector 100, provides the desired flow rate and flow rate control, and has adequate reliability (i.e., an adequate mean time between failures (MTBF)). In one embodiment, pump 112 can be a MEMS or MEMS-based pump, but in other embodiments it need not be MEMS or MEMS-based. Examples of pumps that can be used include small axial pumps (e.g., fans), piston pumps, and electro-osmotic pumps.

Gas chromatograph C, as well as other chromatographs described herein such as chromatographs A, B and A/B, includes a separation column that provides a fluid path from an inlet of the chromatograph to an outlet, and some or all of the walls of the column are coated with a stationary phase coating that can interact with the chemicals being separated by the chromatograph. How thoroughly and how fast chemicals are separated from the gas sample depend on the stationary phase coating, the overall path length of the separation column, and the temperature. For a given stationary phase coating, the longer the separation column the better the chemical spectrum separation, but a long column also extends the separation time. For a given application, the required path length is usually determined by a tradeoff among the coating, the column length, and the temperature.

In one embodiment gas chromatographs used in detector 100 can be MEMS or micro-scale chromatographs, but in other embodiments they need not be micro-scale. In still other embodiments, any gas chromatograph used in detector 100 need not have only one separation column, but can be a cascaded chromatograph with multiple separation columns arranged in series, parallel, or a combination of series and parallel. Moreover, gas chromatograph C can include additional components such as heaters and coolers to heat and/or cool the separation columns (e.g., a thermoelectric cooler such as a Peltier device), temperature sensors, etc.

Controller 120 is communicatively coupled to the individual elements within detector 100 such that it can send control signals and/or receive feedback signals from the individual elements. In one embodiment, controller 120 can be an application-specific integrated circuit (ASIC) designed specifically for the task, for example a CMOS controller including processing, volatile and/or non-volatile storage, memory and communication circuits, as well as associated logic to control the various circuits and communicate externally to the elements of detector 100. In other embodiments, controller 120 can instead be a general-purpose microprocessor in which the control functions are implemented in software. In the illustrated embodiment controller 120 is electrically coupled to the individual elements within detector 100 by conductive traces on the surface or in the interior of substrate 102, but in other embodiments controller 120 can be coupled to the elements by other means, such as optical.

Readout and analysis circuit 118 is coupled to the outputs of gas sensors A-C so that it can receive data signals from gas sensors A-C and process and analyze these data signals. In the illustrated embodiment, readout and analysis circuit 118 is electrically coupled to gas sensors A-C by conductive traces positioned on the surface or in the interior of substrate 102, but in other embodiments it can be coupled to sensors A-C by other means, such as optical means. Readout and analysis circuit 118 is also coupled to controller 120 and can send signals to, and receive signals from, controller 120 so that the two elements can coordinate and optimize operation of detector 100. Although the illustrated embodiment shows controller 120 and readout and analysis circuit 118 as physically separate units, in other embodiments the controller and the readout and analysis circuit could be combined in a single unit.

In one embodiment, readout and analysis circuit 118 can be an application-specific integrated circuit (ASIC) designed specifically for the task, such as a CMOS controller including processing, volatile and/or non-volatile storage, memory and communication circuits, as well as associated logic to control the various circuits and communicate externally. In other embodiments, readout and analysis circuit 118 can instead be a general-purpose microprocessor in which the control functions are implemented in software. In some embodiments readout and analysis circuit 118 can also include signal conditioning and processing elements such as amplifiers, filters, analog-to-digital converters, etc., for both pre-processing of data signals received from gas sensors A-C and post-processing of data generated or extracted from the received data by readout and analysis circuit 118.

In operation of detector 100, when any of sensors A-C is to be used, corresponding pump 112 coupled to its outlet is activated. The running pump draws a gas sample into and through sample conditioner 104 and then into and through sensor A via fluid connection 101. Having been drawn through the relevant sensor, the gas sample is then exhausted by pump 112 into the atmosphere. The relevant sensor analyzes the gas sample and outputs the results to readout and analysis circuit 118. Readout and analysis circuit 118 can communicate the results of the gas analysis to a user, and can also communicate with controller 120 so that, depending on the result, one or more of the other sensors can be activated by the controller depending on the results obtained by earlier-activated sensors. In other embodiments, sensors A-C can be used independently, one at a time or simultaneously in parallel.

FIG. 1B illustrates another embodiment of a gas detector 125. Gas detector 125 is similar to gas detector 100, except in gas detector 125 the elements need not be formed on a substrate, but are grouped into separate gas detection systems A, B, and C: gas detection system A is mode A detection system including mode A sensing; gas detection system B is mode B detection system including mode B sensing; and gas detection system C is mode C detection system including mode C sensing with gas chromatograph C coupled to sensor C. Other embodiments of gas detection systems A, B, or C can include additional components such as sample conditioners 104, additional, chromatographs, valves, etc. (see FIGS. 3-5), and so on. Because they are separate systems, gas detection systems A, B, and C can be mounted in a rack and coupled to an external controller 120 and/or readout and analysis circuit 118 which together can then control the three gas detection systems as shown in FIG. 6A et seq.

Figure 1C:
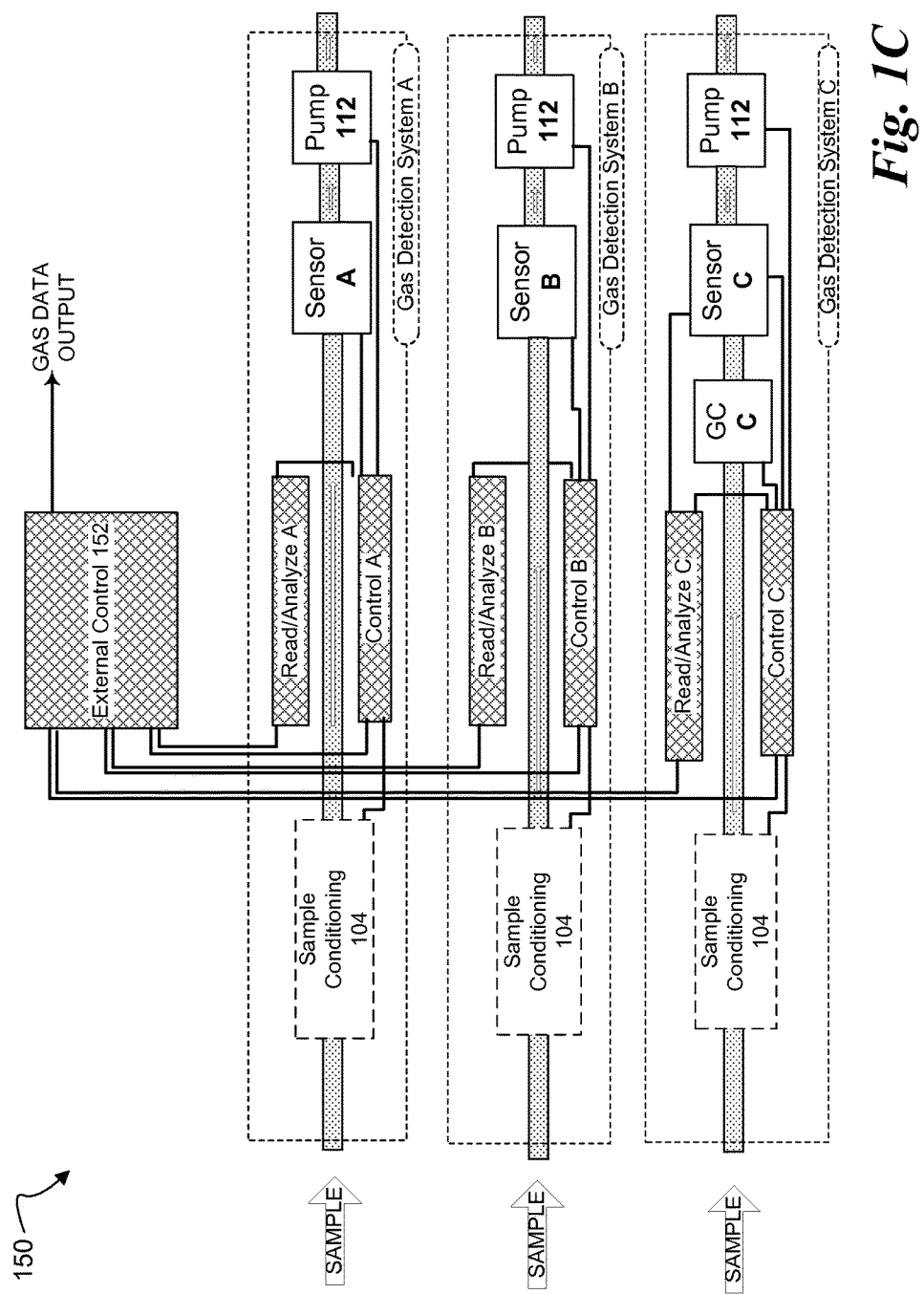

FIG. 1C illustrates another embodiment of a gas detector 150. Gas detector 150 is similar to gas detector 125, but in gas detector 150 the separate gas detection systems A, B, and C are stand-alone systems, each with its own controller and readout and analysis system that can control, read out, and analyze the result obtained by each of the systems. Other embodiments of gas detection systems A, B, or C can include additional components such as sample conditioners 104, additional, chromatographs, valves, etc. (see FIGS. 3-5), and so on. Because they are standalone systems, in gas detector 150 gas detection systems A, B, and C can be mounted in a rack In the illustrated embodiment, the controller and the readout and analysis circuit of each of gas analysis systems A, B, and C is coupled to an external controller 152, which can then monitor the results output by each of gas analysis systems A, B, and C, and coordinate their operation, for example as shown in FIG. 6A et seq.

Figure 1D:
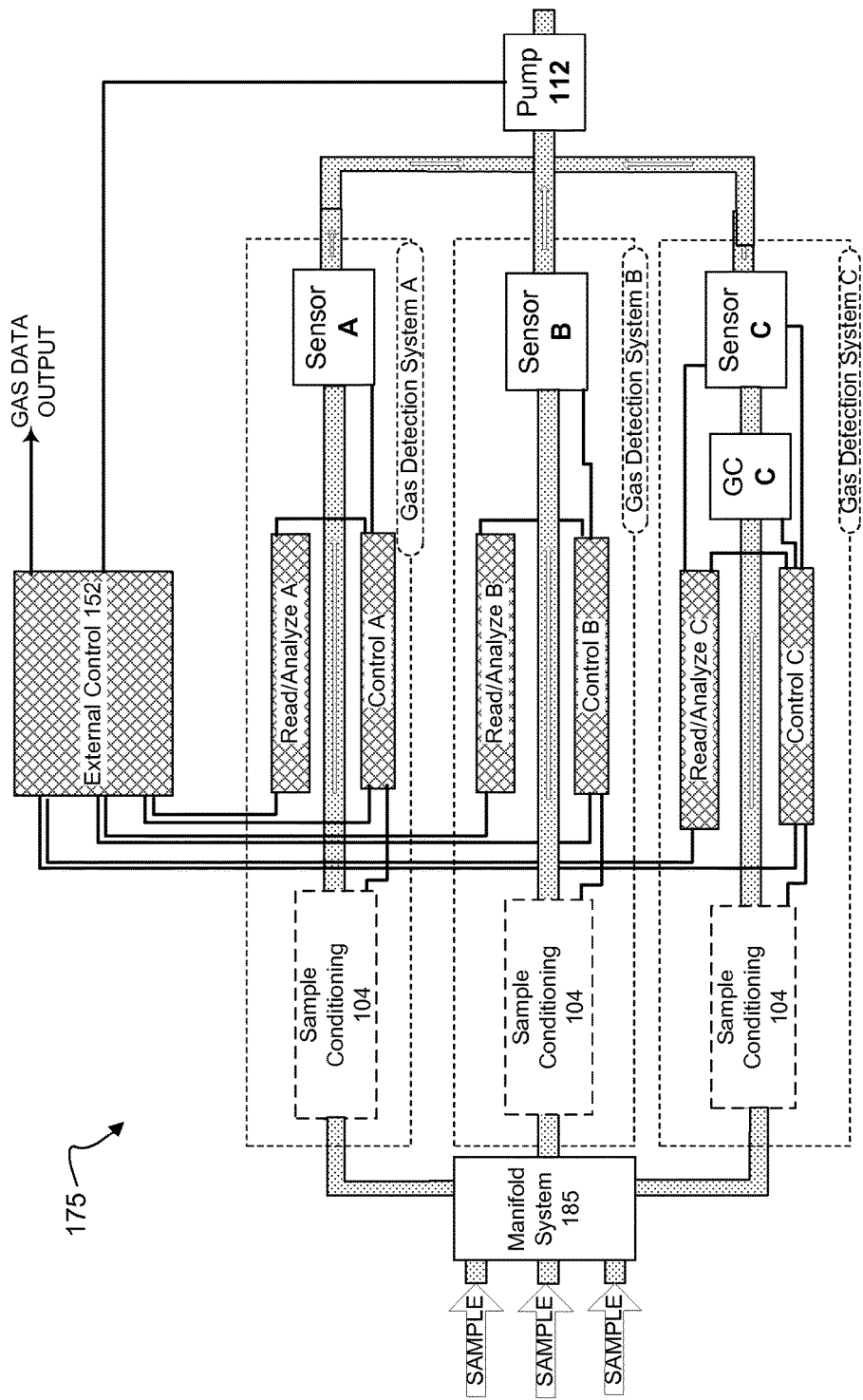

FIG. 1D illustrates another embodiment of a gas detector 175. Gas detector 175 is similar to gas detector 150, but in gas detector 175 the inlets of separate gas detection systems A, B, and C are coupled to a single sample inlet by an optional gas sampling manifold system 185 with single or multiple sample inlets for detection in a single or multiple locations. And, to reduce the number of pumps, the outlets of separate gas detection systems A, B, and C are coupled to a single pump 112 by an outlet manifold. Pump 112 is coupled to external controller 152 to control its operation. As in gas detector 150, other embodiments of gas detection systems A, B, or C can include additional components such as sample conditioners 104, additional, chromatographs, valves, etc. (see FIGS. 3-5), and so on. And, as in gas detector 150, because they are standalone systems gas detection systems A, B, and C can be mounted in a rack or otherwise be separately positioned. In the illustrated embodiment, the controller and the readout and analysis circuit of each of gas analysis systems A, B, and C is coupled to an external controller 152, which can then monitor the results output by each of gas analysis systems A, B, and C, and coordinate their operation, for example as shown in FIG. 6A et seq.

Figure 2:
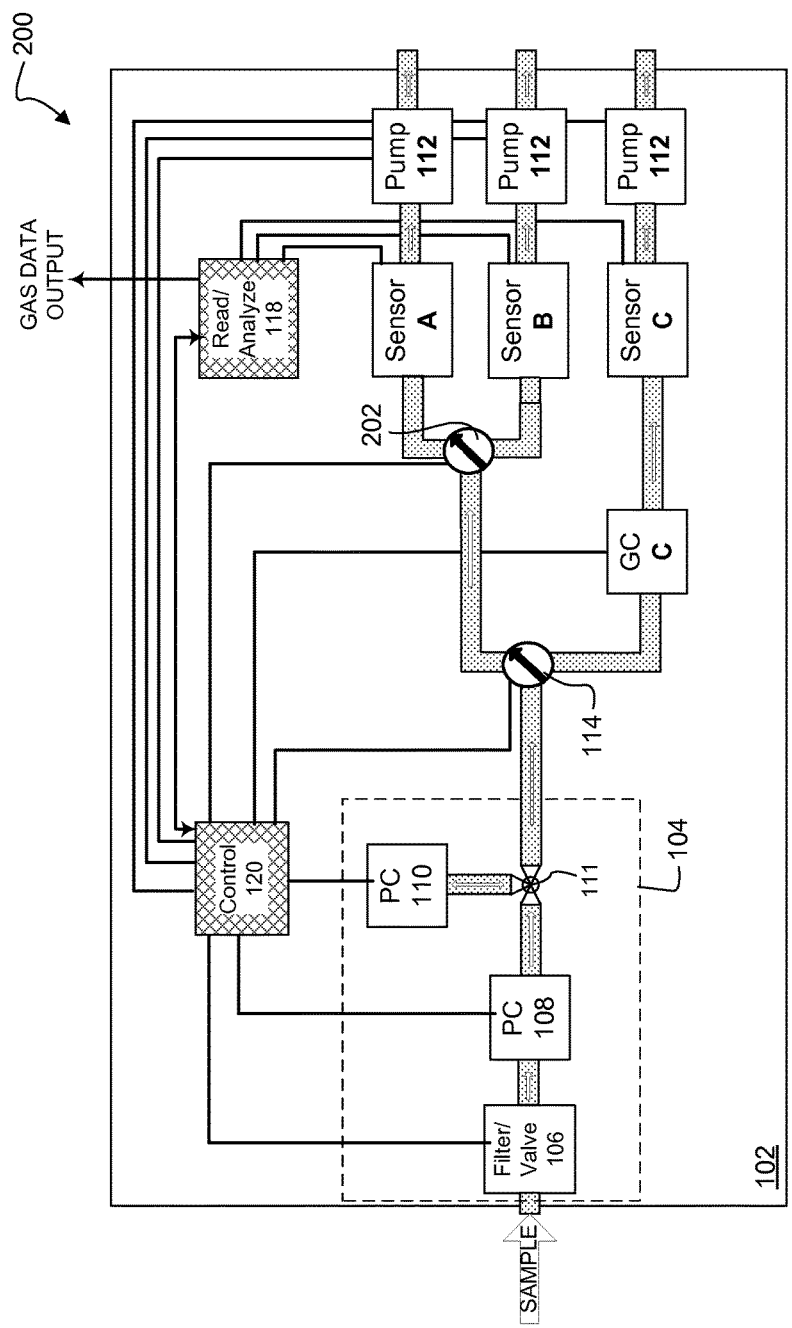
FIG. 2 is a block diagram of another embodiment of a gas detector.

FIG. 2 illustrates an embodiment of a gas detector 200. In some embodiments, it can be useful to reduce the number of components, for example the number of sample conditioners 104, by using a common sample inlet instead of three separate sample inlets as in gas detector 100. Gas detector 200 includes a single sample inlet coupled to a sample conditioner 104, which is optional and can be omitted entirely in other embodiments. Sample conditioner 104 includes a filter/valve unit 106 coupled to the sample inlet, a pre-concentrator 108 coupled to the filter/valve unit, and an optional additional pre-concentrator 110 coupled by valve 111 into the fluid line exiting pre-concentrator 108. All three elements—filter/valve unit 106, pre-concentrator 108, and external pre-concentrator 110—can be coupled to control circuit 120. And, as previously indicated, sample conditioner 104 is optional and can be omitted in other embodiments.

In addition to a filter, filter and valve unit 106 also includes a valve so that further flow into sample conditioning assembly 104 can be stopped once sufficient fluid has passed through the device. Stopping further flow through sample conditioning assembly 104 prevents dilution of gases that will flow out of pre-concentrator 108 during later operation. In other embodiments, filter and valve unit 106 can also include a de-humidifier to remove water vapor from the gas sample and improve the accuracy and sensitivity of downstream detectors. In embodiments where the gas sample contains no particulates, for instance because it has been pre-filtered, the filter portion of filter and valve unit 106 can be omitted.

Pre-concentrator 108 receives fluid from filter and valve unit 106 and outputs fluid through three-way valve 111 to multi-way valve 114. As fluid flows through pre-concentrator 108, the pre-concentrator absorbs certain chemicals from the passing fluid, concentrating those chemicals for later separation and/or detection. In one embodiment of device 200 pre-concentrator 108 can be a MEMS pre-concentrator, but in other embodiments pre-concentrator 106 can be a non-MEMS chip scale device.

Sample conditioner 104 includes provisions for an external pre-concentrator 110 (i.e., a pre-concentrator not mounted on substrate 102). In the embodiment shown, three-way valve 111 is placed in the fluid connection pre-concentrator 106 and valve 114. Valve 111 allows use of external pre-concentrator 110 instead of, or in addition to, pre-concentrator 108. In one embodiment external pre-concentrator 110 can be a breath collection bag, but in other embodiments it can be something different. In an alternative embodiment pre-concentrator 108 can be permanently removed and replaced by external pre-concentrator 110; in an embodiment where external pre-concentrator 110 replaces pre-concentrator 108 external pre-concentrator 110 can be coupled upstream of the filter and valve unit 106.

Sample conditioner 104 is coupled to valve 114. Valve 114 is a multi-way valve coupled to control circuit 120 so that it can be selectively activated by the control circuit to direct the gas sample to sensors A, B, or C. Although illustrated as a single valve, in different embodiments valve 114, as well as other valves described herein, can be a single valve or a combination of valves that can direct the gas sample to each of sensor A-C individually, to all sensors A-C simultaneously, or to a subset the includes less than all sensors. If valve 114 is adjusted to direct the sample gas to sensor C, sample gas travels through gas chromatograph (GC) C, through sensor C, through pump 112, and out to the atmosphere. If valve 114 is activated to direct the sample gas to sensors A and B, the sensor the sample gas encounters a further multi-way valve 102 which is also coupled to control circuit 120 so that it can be selectively activated to direct sample gas to sensor A or sensor B.

Figure 3:
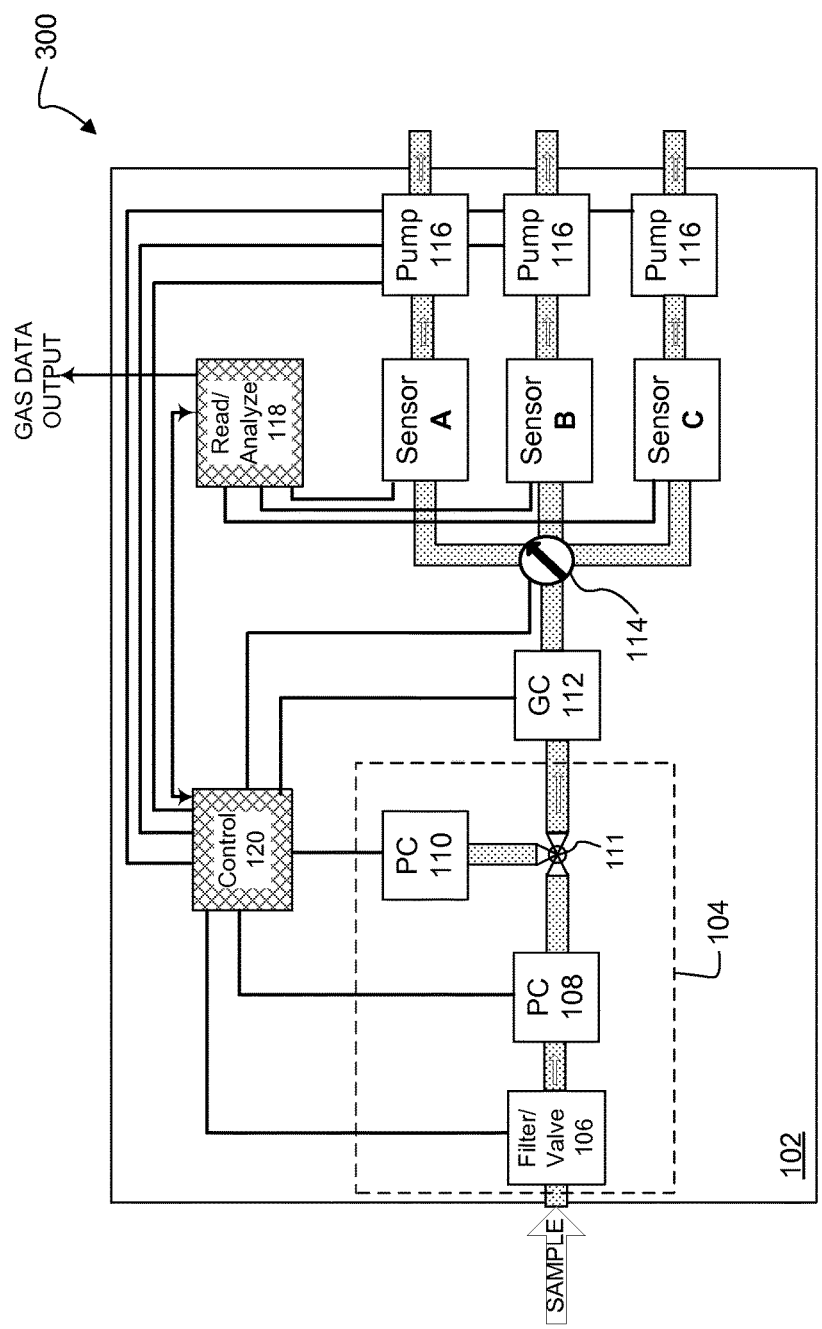
FIG. 3 is a block diagram of another embodiment of a gas detector.

FIG. 3 illustrates an embodiment of a gas detector 300. Detector 300 is similar in most respects to gas detector 200. The primary difference between detectors 200 and 300 is that in detector 300 a multi-way valve 114 is coupled to control circuit 120 to direct the gas sample to any of sensors A-C, instead of using two multi-way valves as in detector 200. Although illustrated as a single valve, in different embodiments valve 114, as well as other valves described herein, can be a single valve or a combination of valves that can direct the gas sample to each of sensors A-C individually, to all sensors A-C simultaneously, or to a subset the includes less than all sensors. Also, in gas detector 300 a gas chromatograph 112 is coupled in the fluid connection upstream of valve 114, so that all sensors A-C share a gas chromatograph—in other words, there is a one-to-many correspondence between gas chromatograph and sensors. With this arrangement, any sensor selected by valve 114 receives a gas sample with some prior separation of chemical species. In another embodiment of detector 300 chromatograph 112 can be omitted, which would make gas detector 300 similar to gas detector 200 but with a different valve arrangement for directing the gas sample to the different sensors.

Figure 4:
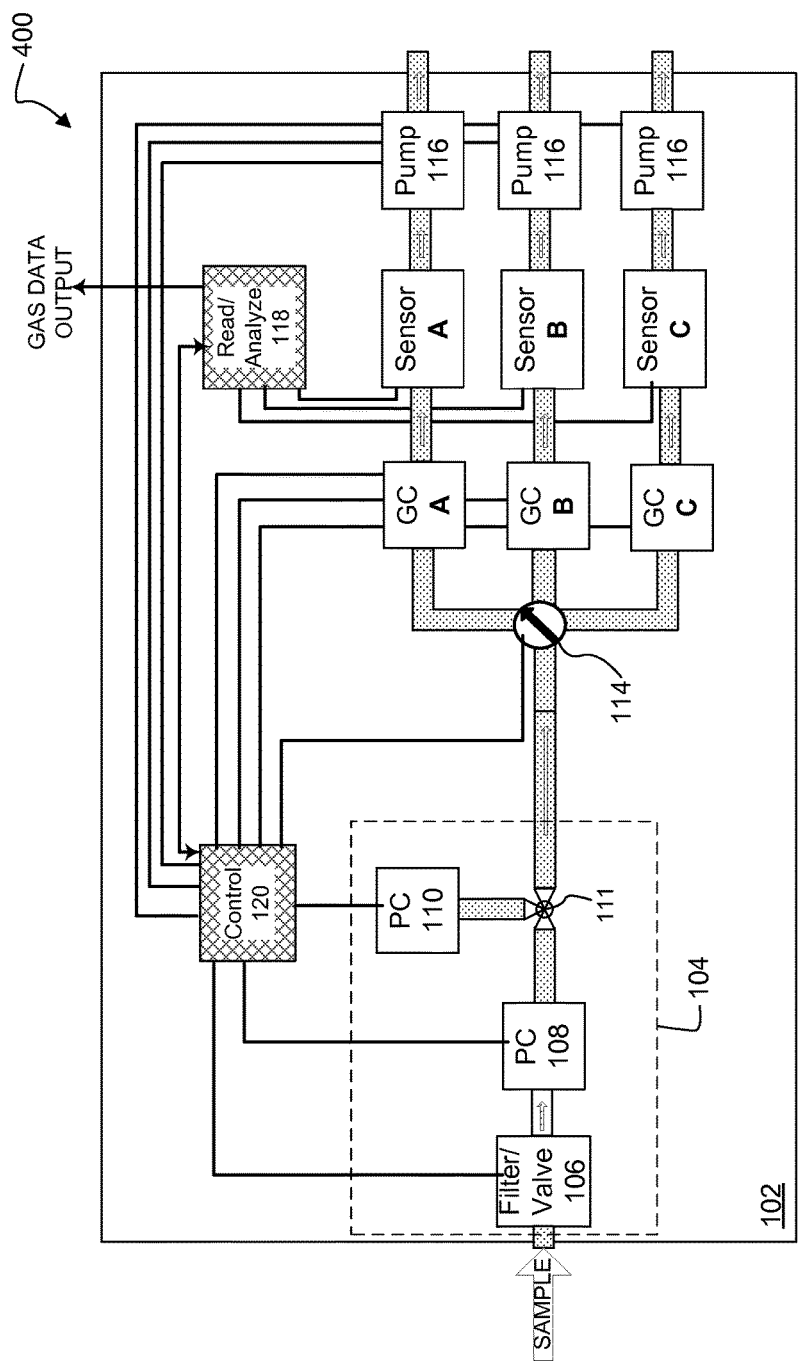
FIG. 4 is a block diagram of another embodiment of a gas detector.

FIG. 4 illustrates an embodiment of a gas detector 400. Detector 400 is similar in most respects to gas detector 300, except that gas chromatograph 112 is removed from upstream of valve 114 and instead gas chromatographs are put in every line downstream of valve 114, between the valve and the individual gas sensors, so that there is a one-to-one correspondence between gas chromatographs and sensors. Hence, gas chromatograph A is paired with sensor A, gas chromatograph B is paired with sensor B, and gas chromatograph C is paired with sensor C. With this arrangement there is some separation of chemical species before sensing, but the separated species or degree of separation can be different for each sensor.

Figure 5:
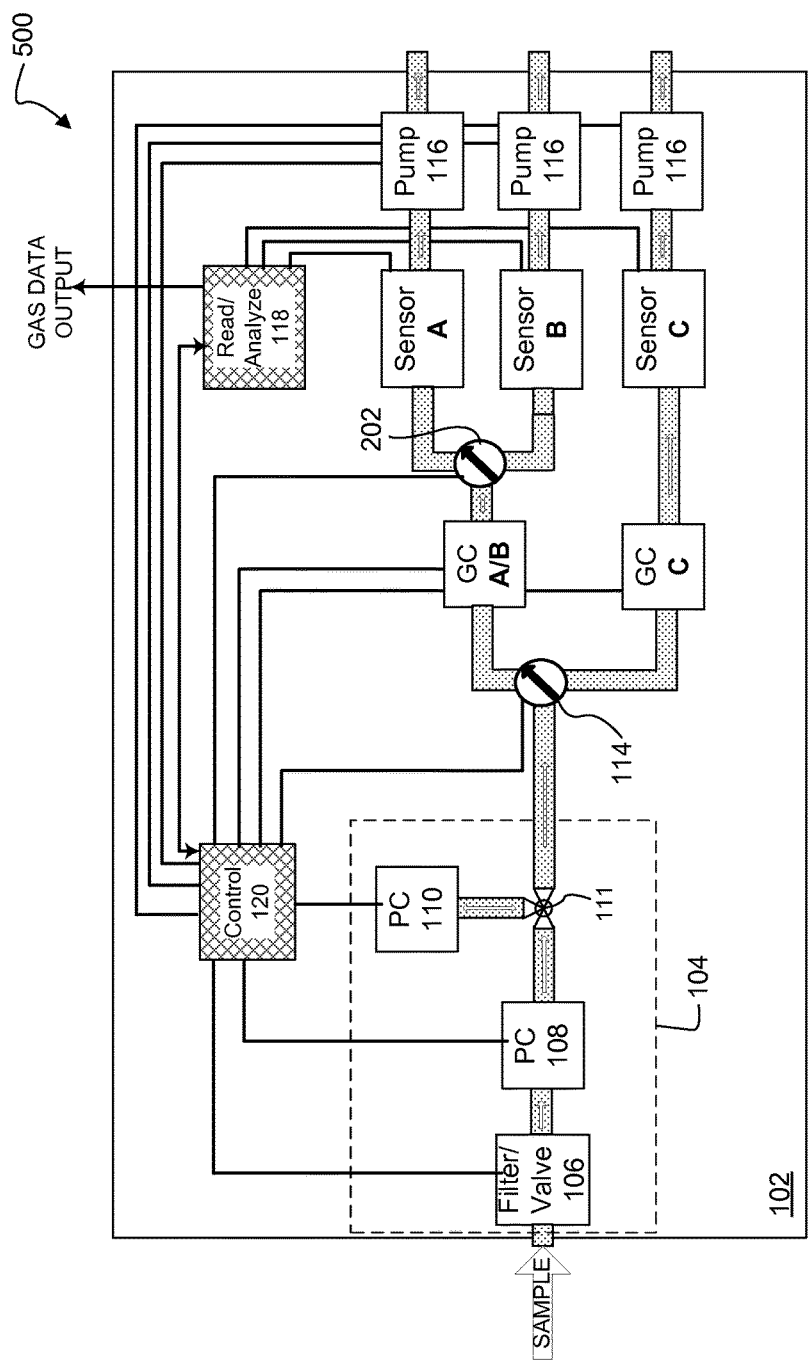
FIG. 5 is a block diagram of another embodiment of a gas detector.
Figure 6A:
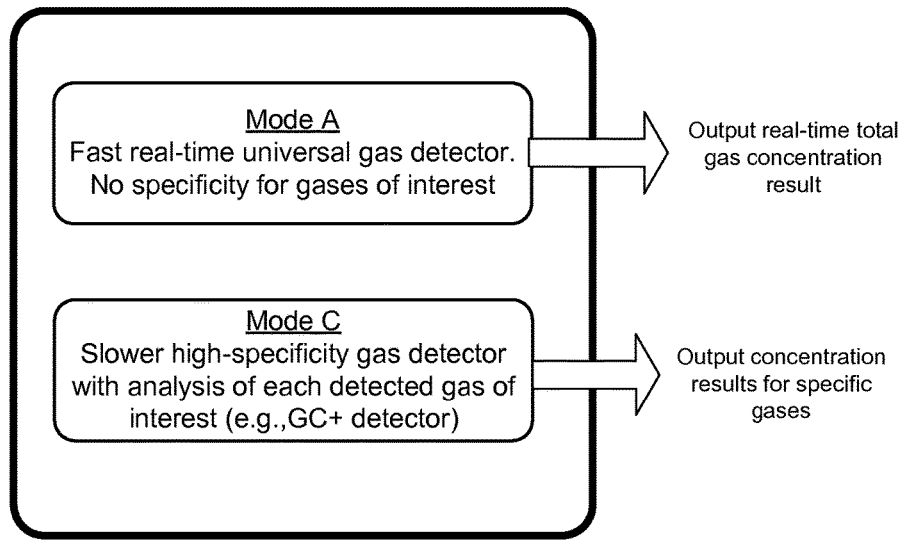
FIGS. 6A-6D are flowcharts of embodiments of processes for two-mode operation of a gas detector.

FIG. 5 illustrates an embodiment of a gas detector 500. Gas detector 500 is similar to gas detector 200. The primary difference is that detector 500 includes an additional gas chromatograph (GC A/B) positioned between valves 114 and 202, so that sensors A and B share one chromatograph. Hence gas detector 500 has both one-to-one and one-to-many correspondences between sensors and gas chromatographs.

FIGS. 6A-6D illustrate embodiments of two-sensor operation of any of the previously-described embodiments of gas detectors. All the gas detector embodiments described above include three sensors, but in any of the described embodiments one of the sensors can be omitted. Alternatively, in an embodiment that includes three gas sensors only two need be used. Mode A results can produce much faster real-time detection result on total gas concentration for early warning on gas excursion. Mode B results (with a slightly longer analysis time than mode A), if obtained, can provide additional information on certain group of gases that contribute to the gas concentration excursion. And Mode C results (which require longer analysis time than modes A or B), if obtained, can produce more detailed individual concentration of specific gases that might be causing the excursions detected by mode A or mode B.

FIG. 6A illustrates an embodiment in which a mode A sensor and a mode C sensor operate independently, whether one at a time or simultaneously in parallel. The mode A sensor is a fast real-time universal gas detector with no specificity for the gases of interest, which outputs a real-time in total gas concentration results. The mode C sensor is a slower high-specificity gas detector with analysis of each detected gas of interest, and outputs concentration results for specific gases. While the mode A sensor and mode C sensor can operate at their own cycling frequencies respectively, one sensor's test result can be used to trigger and start the other sensor's operation, but a fast mode sensor can keep cycling without waiting for the result from a slow mode sensor. For example, the mode A sensor may be first started in repeating gas sensing cycles while the mode C sensor is not activated. When the mode A result satisfies certain criteria, the control electronics can activate the mode C sensor to start its detection cycle. Both sensors can be operating in parallel or in sequence until the repeating sensing cycle of either sensor is de-activated by the control electronics based on certain criteria.

Figure 6B:
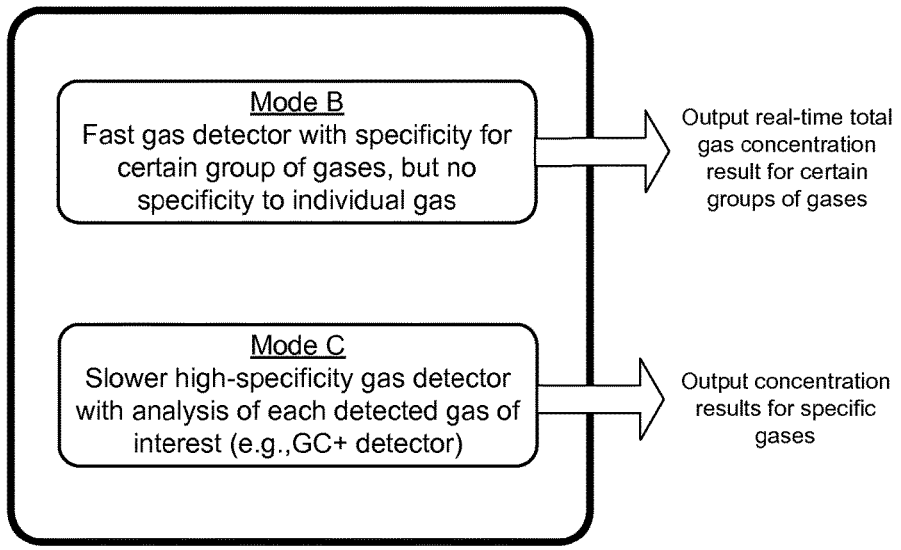

FIG. 6B illustrates an embodiment in which a mode B sensor and a mode C sensor operate independently, whether one at a time or simultaneously in parallel. The mode B sensor is a fast gas detector with specificity for certain groups of gases, but no specificity to an individual gas. The mode B sensor outputs real-time total gas concentration results for certain groups of gases. The mode C sensor, as before, is a slower high-specificity gas detector with an analysis of each detected gas of interest that outputs concentration results for specific gases. Similar to FIG. 6A, while mode B sensor and mode C sensor can operate at their own cycling frequencies respectively, one sensor's test result can be used to trigger and start the other sensor's operation, but a fast mode sensor can keep cycling without waiting for the result from a slow mode sensor. For example, the mode B sensor may be first started in repeating gas sensing cycles while mode C sensor is not activated. When the mode B result satisfies certain criteria, the control electronics actives mode C sensor to start its detection cycle. Both sensors can be operating in parallel or in sequence until the repeating sensing cycle of either sensor is de-activated by the control electronics based on certain criteria.

Figure 6C:
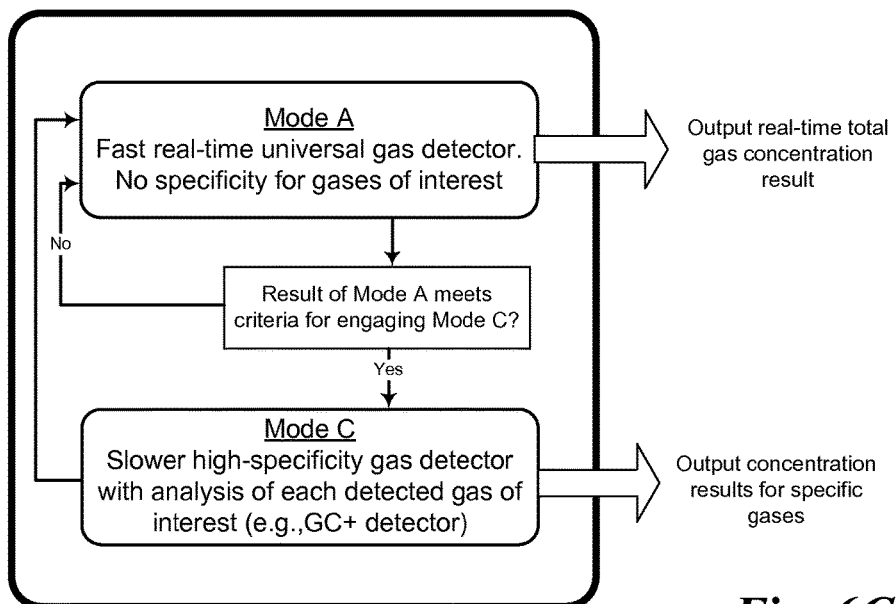
Figure 6D:
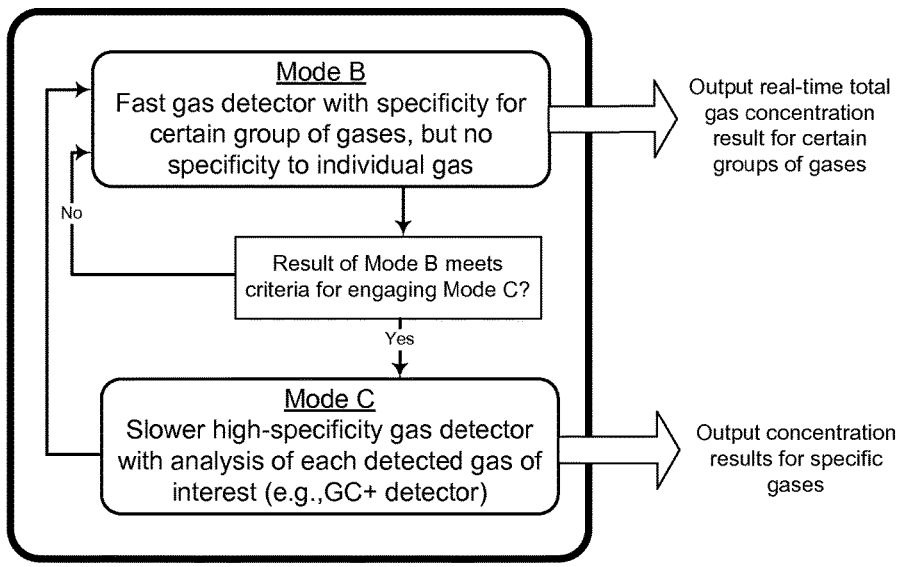

FIGS. 6C-6D illustrate embodiments of a process for two-sensor operation of any of the previously-described embodiments of gas detectors. In the illustrated embodiments, activation or engagement of one sensor depends upon the results obtained from another sensor but, as noted above, a fast mode sensor can keep cycling without waiting for a result from a slow mode sensor. FIG. 6C illustrates an embodiment with a mode A sensor and a mode C sensor. The mode A sensor, as before, is a fast real-time universal gas detector with no specificity for gases of interest that outputs real-time total gas concentration results. After operating the mode A sensor, the process checks whether the mode A results meet the criteria for activating or engaging the mode C sensor: if the mode A results don't meet the criteria for activating the mode C sensor the process reverts to operation of the mode A sensor, but if the mode A results do meet the criteria for engaging the mode C sensor, the process engages or activates the mode C sensor. As before, the mode C sensor is a slower high-specificity gas detector that analyzes each detected gas of interest and, if engaged, outputs concentration results for specific gases. After the mode C sensor completes its analysis, the process reverts to operating the mode A sensor.

FIG. 6D illustrates an embodiment with a mode B sensor and a mode C sensor. The mode B sensor, as before, is a fast gas detector with specificity for certain groups of gases, but no specificity to an individual gas; it outputs real-time total gas concentration results for certain groups of gases. After operating the mode B sensor, the process checks whether the mode B results meet the criteria for activating or engaging the mode C sensor: if the mode B results don't meet the criteria for activating the mode C sensor the process reverts to operation of the mode B sensor, but if the mode B results do meet the criteria for engaging the mode C sensor, the process engages or activates the mode C sensor. As before, the mode C sensor is a slower high-specificity gas detector that analyzes each detected gas of interest and, if engaged, outputs concentration results for specific gases. After the mode C sensor completes its analysis, the process reverts to operating the mode B sensor.

FIGS. 7A-7D illustrate embodiments of three-sensor operation of any of the previously-described embodiments of gas detectors. Mode A results can produce much faster real-time detection result on total gas concentration for early warning on gas excursion. Mode B results (with a slightly longer analysis time than mode A), if obtained, can provide additional information on certain group of gases that contribute to the gas concentration excursion. And Mode C results (which require longer analysis time than modes A or B), if obtained, can produce more detailed individual concentration of specific gases that might be causing the excursions detected by mode A or mode B.

Figure 7A:
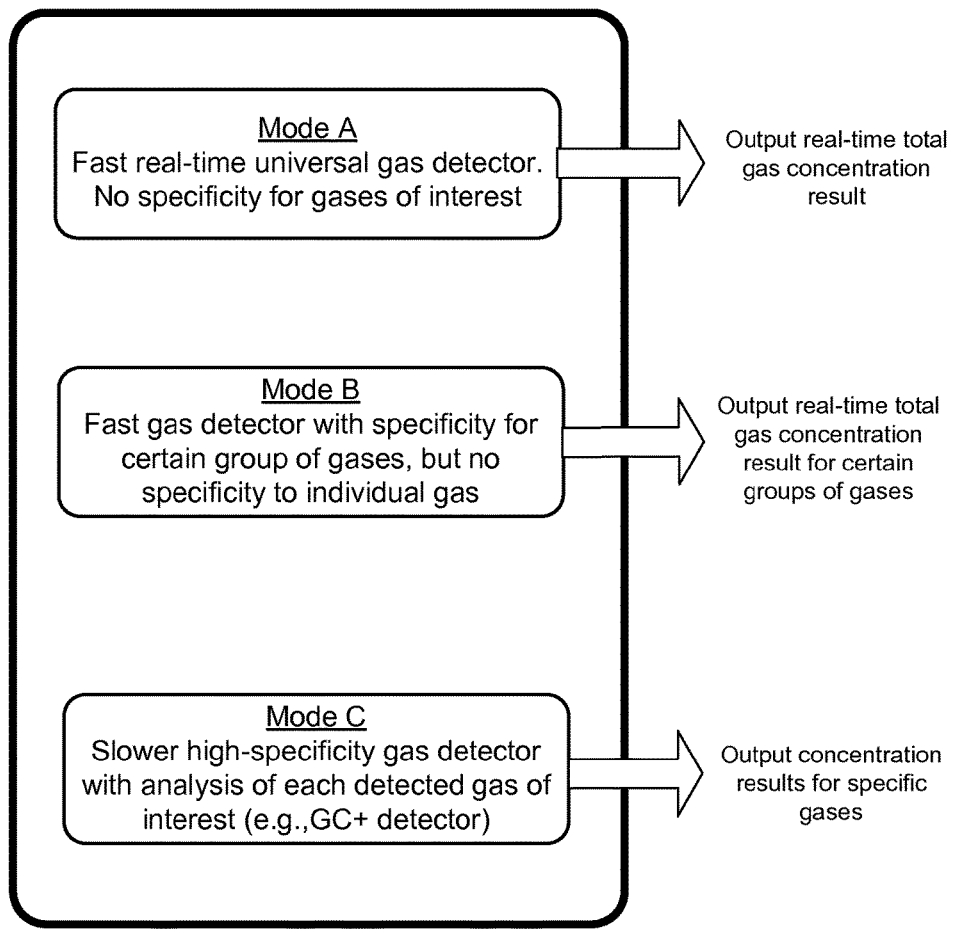
FIGS. 7A-7D are flowcharts of embodiments of processes for three-mode operation of a gas detector.

FIG. 7A illustrates an embodiment of three-sensor operation of any of the previously-described embodiments of gas detectors. In the illustrated embodiment a mode A sensor, a mode B sensor, and a mode C sensor operate independently, one at a time or simultaneously in parallel. The mode A sensor is a fast real-time universal gas detector with no specificity for gases of interest, which outputs a real-time total gas concentration results. The mode B sensor is a fast gas detector with specificity for certain groups of gases, but no specificity to an individual gas; it outputs real-time total gas concentration results for certain groups of gases. The mode C sensor is a slower high-specificity gas detector with an analysis of each detected gas of interest, and outputs concentration results for specific gases. Similar to FIG. 6A and FIG. 6B, while mode A, mode B sensor and mode C sensor can operate at their own cycling frequencies respectively, one sensor's test result can be used to trigger and start another sensor's operation, but a fast mode sensor can keep repeating its sensing cycle without waiting for the result from a slow mode sensor. Three sensors can be operating in parallel or in sequence until the repeating sensing cycle of any sensor is de-activated by the control electronics based on certain criteria.

Figure 7B:
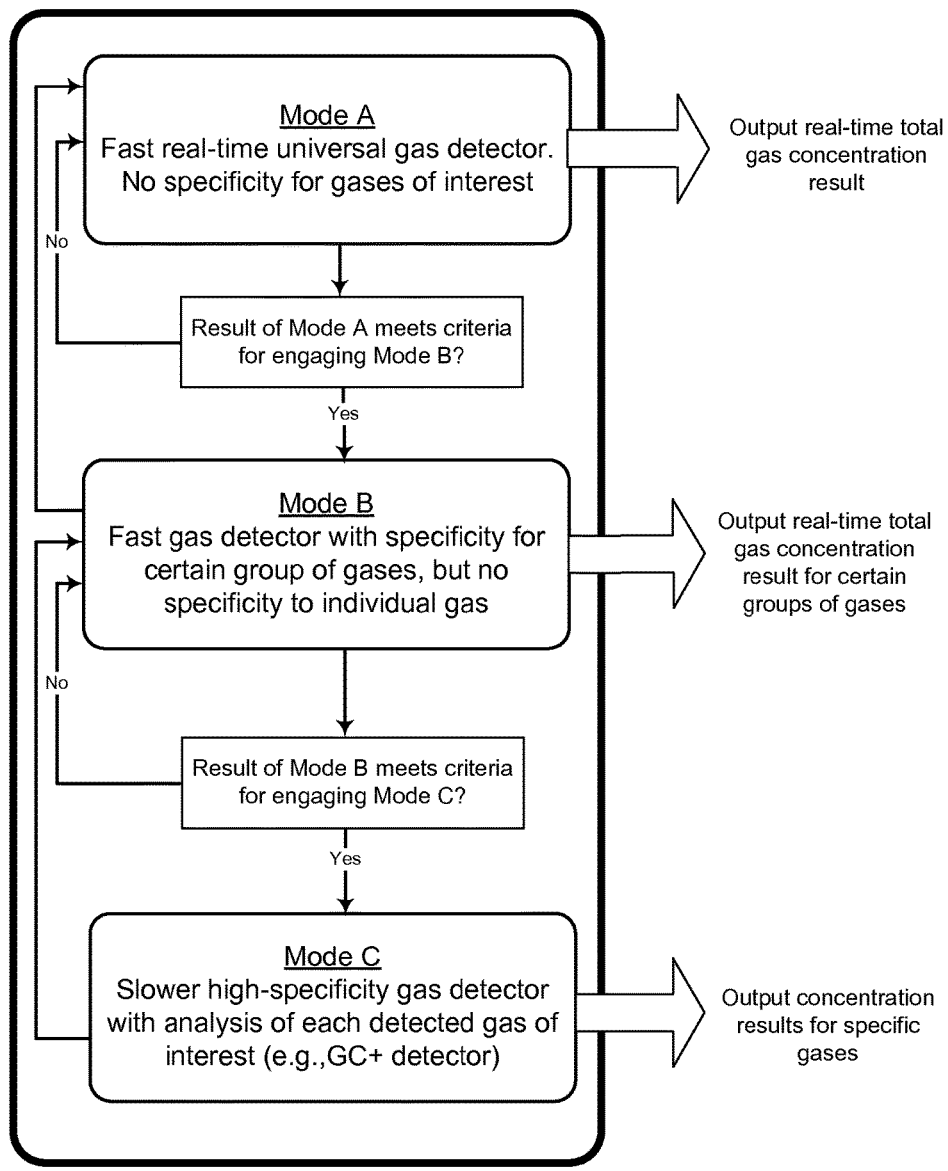
Figure 7C:
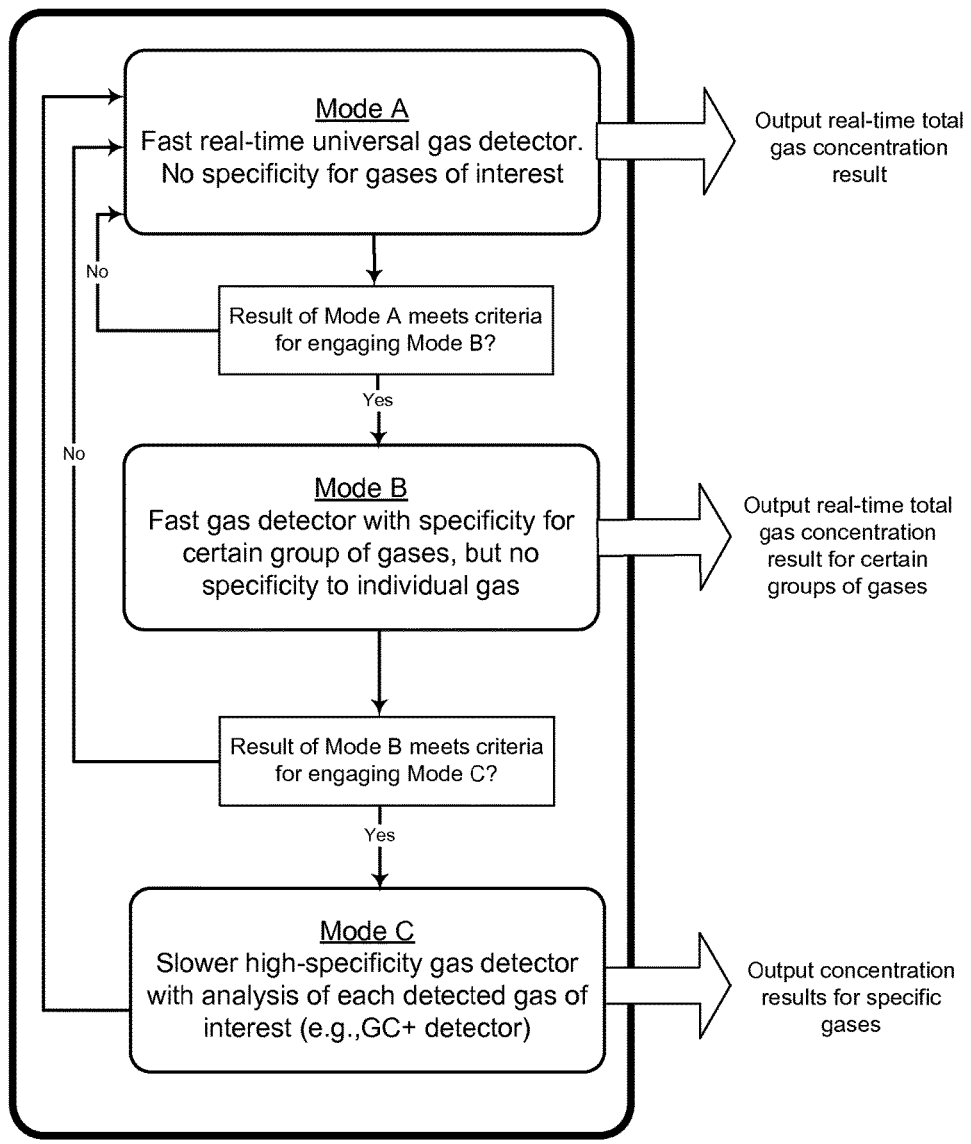
Figure 7D:
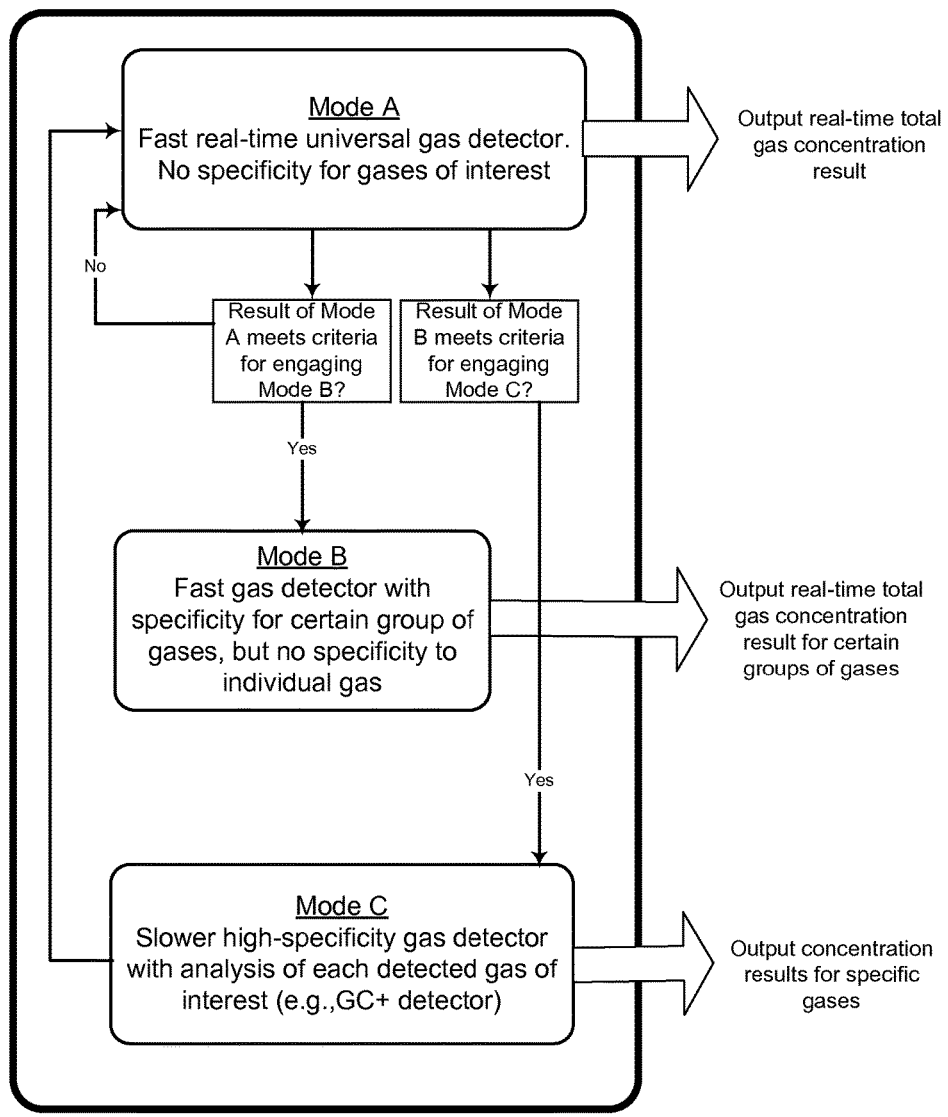

FIGS. 7B-7D illustrate embodiments of three-sensor operation of any of the previously-described embodiments of gas detectors. In the illustrated embodiments, activation or engagement of one gas sensor depends upon the results obtained from another gas sensor but, as noted above, a fast mode sensor can keep repeating its sensing cycle without waiting for a result from a slow mode sensor. FIG. 7B illustrates an embodiment with mode A, mode B, and mode C sensors as in FIG. 7A. But in this embodiment, after operation of the mode A sensor the process checks whether the mode A results meet the criteria for activating or engaging the mode B sensor: if they don't the process reverts to operating the mode A sensor, but if they do the process activates or engages the mode B sensor. If the mode B sensor is activated, after operation of the mode B sensor the process checks whether the mode B results meet the criteria for activating or engaging the mode C sensor: if they don't the process reverts to operating the mode B sensor, but if they do the process activates or engages the mode C sensor, outputs the mode C results, and reverts to operating the mode B sensor.

FIG. 7C illustrates an embodiment with mode A, mode B, and mode C sensors as in FIG. 7A. In this embodiment, after operation of the mode A sensor the process checks whether the mode A results meet the criteria for activating or engaging the mode B sensor: if they don't the process reverts to operating the mode A sensor, but if they do the process activates or engages the mode B sensor. If the mode B sensor is activated, after operation of the mode B sensor the process checks whether the mode B results meet the criteria for activating or engaging the mode C sensor: if they don't the process reverts to operating the mode A sensor, but if they do the process activates or engages the mode C sensor, outputs the mode C results, and reverts to operating the mode A sensor.

FIG. 7D illustrates an embodiment with mode A, mode B, and mode C sensors as in FIG. 7A. In this embodiment, after operation of the mode A sensor the process checks whether the mode A results meet the criteria for activating or engaging one or both of the mode B sensor and the mode C sensor. If the criteria for activating the mode B sensor are met, the process activates the mode B sensor and outputs the mode B results. And if the criteria for activating the mode C sensor are met the process activates the mode C sensor, outputs the mode C results, and reverts to operating the mode A sensor.

The above description of illustrated embodiments of the invention, including what is described in the abstract, is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize. These modifications can be made to the invention in light of the above detailed description.

The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

The invention claimed is:

1. A gas detector comprising:
   a first gas sensor having a fluid inlet for receiving a gas sample and a fluid outlet for exhausting the gas sample, the first sensor having a first gas specificity and a first response time;
   a second gas sensor having a fluid inlet for receiving the gas sample and a fluid outlet for exhausting the gas sample, the second sensor having a second gas specificity and a second response time, wherein the first gas specificity is different than the second gas specificity, the first response time is different than the second response time, or both the first gas specificity and the first response time are different than the second gas specificity and the second response time;
   a readout and analysis circuit coupled to the first and second gas sensors to read and analyze data from the first and second gas sensors; and
   a control circuit coupled to the readout and analysis circuit and to the first and second gas sensors, wherein the control circuit can execute logic that operates the first gas sensor, the second gas sensor, or both the first and second gas sensors.

2. The gas detector of claim 1 wherein the first gas sensor is a fast-response low-specificity sensor and the second gas sensor is a fast-response partial-specificity sensor.

3. The gas detector of claim 1 wherein the first gas sensor is a fast-response partial-specificity sensor and the second gas sensor is a slow-response high-specificity sensor.

4. The gas detector of claim 1 wherein the control circuit operates the first gas sensor independently of the second gas sensor.

5. The gas detector of claim 1 wherein the control circuit operates the second gas sensor if the result obtained from the first gas sensor meets specified criteria for activating the second gas sensor.

6. The gas detector of claim 1, further comprising a third gas sensor having a fluid inlet for receiving the gas sample and a fluid outlet for exhausting the gas sample, the third sensor having a third gas specificity and a third response time and being coupled to the control circuit.

7. The gas detector of claim 6 wherein:
the first gas sensor is a fast-response low-specificity sensor,
the second gas sensor is a fast-response partial-specificity sensor, and
the third gas sensor is a slow-response high-specificity sensor.

8. The gas detector of claim 6 wherein the control circuit operates the first, second, and third gas sensors independently.

9. The gas detector of claim 8 wherein the detector is coupled to a gas sampling manifold with single or multiple inlets for sampling from multiple locations.

10. The gas detector of claim 6 wherein the control circuit operates the second gas sensor if the result obtained from the first gas sensor meets specified criteria for activating the second gas sensor.

11. The gas detector of claim 10 wherein the control circuit returns to operation of the first gas sensor when the second gas sensor has completed its sensing.

12. The gas detector of claim 10 wherein the control circuit operates the third gas sensor if the second gas sensor was operated and if the result obtained from the second gas sensor meets specified criteria for activating the third gas sensor.

13. The gas detector of claim 12 wherein the control circuit returns to operation of the first gas sensor or the second gas sensor when the third gas sensor has completed its sensing.

14. The gas detector of claim 6 wherein the control circuit can select the second gas sensor or the third gas sensor, depending on whether the result obtained from the first gas sensor meets specified criteria for operating the second gas sensor or meets specified criteria for activating the third gas sensor.

15. The gas detector of claim 14 wherein the control circuit returns to operation of the first gas sensor when the second gas sensor has completed its sensing or returns to operation of the second gas sensor when the third gas sensor has completed its sensing.

* * * * *